US005639905A

United States Patent [19]

Nagy et al.

[11] Patent Number: 5,639,905
[45] Date of Patent: Jun. 17, 1997

[54] PROCESS FOR PREPARING N-PHENYL-N-METHOXYACETYL-DL-ALANINE METHYL ESTER DERIVATIVES

[75] Inventors: Lajos Nagy; Jenö Pelyva, both of Füzfögyártelep; Pál Agócs; Csaba Söptei, both of Veszprém; Judit Benczik née Pásztor, Balatonalmádi; Zoltán Kolonics, Veszprém; Sándor Bálint, Balatonalmádi; Dezsö Sebök; Jolán Cseke, both of Veszprém; Tibor Kránitz, Balatonalmádi; László Légrádi, Füzfögyártelep, all of Hungary

[73] Assignee: Nitrokémia Ipartelepek, Hungary

[21] Appl. No.: 368,271

[22] Filed: Sep. 13, 1994

Related U.S. Application Data

[63] Continuation of PCT/HU93/00017, Mar. 24, 1993.

[30] Foreign Application Priority Data

Mar. 27, 1992 [HU] Hungary .................... 1020/92

[51] Int. Cl.⁶ .................................................. C07C 269/04
[52] U.S. Cl. .................................................. 560/29
[58] Field of Search .................................................. 560/29

[56] References Cited

U.S. PATENT DOCUMENTS 3,048,626 8/1962 Wallingford ............................ 560/29
3,780,090 12/1973 Akiba et al. ............................ 560/29

FOREIGN PATENT DOCUMENTS 0045049 2/1982 European Pat. Off. ...... C07C 103/48
3010412 9/1980 Germany .
0607888 12/1978 Switzerland .................... A01N 9/20

*Primary Examiner*—Joseph Conrad
*Attorney, Agent, or Firm*—Schweitzer Cornman Gross & Bondell LLP

[57] ABSTRACT

Process for the preparation of N-phenyl-N-methoxyacetyl-DL-alanine methyl ester derivatives of the formula (I).

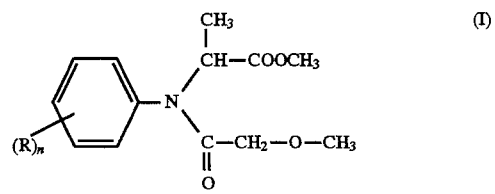

wherein R is a $C_{1-4}$ alkyl residue; and n is a cardinal number between from 1 to 3, which comprises reacting an N-methoxyacetyl derivative of the formula (II).

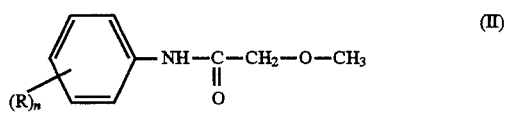

wherein R and n are as defined above, with a stoichiometric amount of an alkaline metal alkoxide, at a temperature between 80° C. and 150° C., until completion of the removal of the alkanol present in the system, then reacting the thus obtained alkaline metal salt of the compound of formula (II) directly or after isolation with a methyl DL-x-halopropionate.

6 Claims, No Drawings

PROCESS FOR PREPARING N-PHENYL-N-METHOXYACETYL-DL-ALANINE METHYL ESTER DERIVATIVES

This is a continuation of PCT/HU93/0017, filed Mar. 24, 1993.

This invention relates to an improved process for preparing the derivatives of N-phenyl-N-methoxyacetyl-DL-alanine methyl-ester of the formula (I), wherein the substituents R of the optionally substituted phenyl group may be straight or branched chain $C_{1-4}$alkyl groups.

The derivatives of N-phenyl-N-methoxyacetyl-DL-alanine methyl ester are substances possessing a known biological activity: several of them exert a fungicidal effect. The most known member of this compound class is N-(2,6-dimethylphenyl)-N-methoxyacetyl-DL-alanine methyl ester (trade name: metalaxyl), the fungicidal properties of which were described by F. J. Schwinn et al./Mitt. Biol. Bundesanst. Land-Forstswiertsch. Berlin-Dahlem 178, 145 (1977)/. This compound is the active ingredient of several fungicidal compositions used in various agrarian cultures against infections induced by mildew (*peronospora*), *Phytophtora infestans*, *Plasmopara viticola* and the like.

The preparation of metalaxyl is published in the CH-PS 607,888, according to which 2,6-dimethylaniline is first reacted with methyl DL-α-bromopropionate in the presence of sodium hydrogen carbonate as acid binding agent, then methyl N-(2,6-dimethylphenyl)-DL-alaninate thus obtained is acylated with methoxyacetyl chloride to give metalaxyl.

A drawback of the known process consists therein that, partly due to the hydrolyzing effect of water arising from a side reaction, the yield is low, the alkylating agent, i.e. the DL-α-bromopropionate ester has to be employed in a several-fold excess and a considerable amount of organic wastes loading the environment is formed during the accomplishment of the process on an industrial scale.

According to the process described in the HU-PS 202,481, after acylating 2,6-dimethylaniline with methoxyacetic acid, the N-methoxyacetyl-2,6-dimethylaniline obtained is heated together with a twofold excess of methyl DL-α-bromopropionate to 120° C., and after adding sodium methoxide in small portions to the reaction mixture obtained, the alkylation is carried out at 140° C.

The drawback of this latter process lies therein that methyl DL-α-bromopropionate reacts not only with 2,6-dialkylaniline but also with sodium methoxide being present to give the methoxy ester derivative. As a consequence of this side reaction, the reactants should be used in a significant excess, a fact also shown thereby that both methyl DL-α-bromopropionate and sodium methoxide, respectively are used in a twofold quantity of the theoretical (calculated) amount. Thus, a twofold amount of sodium bromide side product is formed, a half part of the alkylating agent, i.e. methyl DL-α-bromopropionate is lost to give rise to a waste and in addition, the aimed end product becomes more contaminated.

A purpose of the present invention is to develop a process being free from the above drawbacks and making possible to prepare derivatives of N-(2,6-dialkylphenyl)-N-methoxyacetyl-DL-alanine methyl ester on an industrial scale in a way, which the environment becomes less contaminated by.

It has been found that N-methoxyacetyl-2,6-dialkylanilines can be alkylated in a very good yield by using methyl DL-α-halopropionate in a half or third amount in relation to the processes known in the art in such a manner that an alkaline metal salt of the N-methoxyacetyl-2,6-dialkylaniline is reacted with methyl DL-α-halopropionate, optionally in an organic solvent, a temperature between -20° C. and +50° C., preferably at 25° to 35° C. When carrying out the alkylation on the basis of this recognition, the simultaneous presence of any acid binding agent is unnecessary therefore, no competitive side reaction occurs and the target product can be obtained in a highly pure state and better yields can be attained than by using processes known in the art.

This recognition is unexpected and surprising because the simultaneous presence of an acid binding agent has been distinctly required in the processes known. This was accompanied in each case by a side reaction deteriorating the yield, increasing the required amounts of reactants, contaminating the final product and enhancing the amount of wastes.

The alkaline metal salts of N-methoxyacetyl-2,6-dialkylanilines which are starting substances of the process according to the invention and make possible to alkylate without any acid binding agent, are novel compounds, the preparation and properties of which cannot be found in the literature. Although it is mentioned in the Hungarian patent specification No. 202,481 that the alkylating reaction proceeds through the sodium salt of N-methoxyacetyl-2,6-dialkylaniline, however, no reference to the preparation or existence thereof can be traced. As a result of the processes known in the art for the preparation of metalaxyl, the alkylation gave an acceptable yield even at higher temperatures (at 120°–140° C.) only by using a considerable excess (2- or 3-fold of the stoichiometric amount) of the alkylating agent in the presence of an acid binding agent. No process has been known in the literature which would result metalaxyl in a very good yield by using a stoichiometric amount of methyl-DL-α-halopropionate at temperature between -20° C. and +50° C. with or without the addition of an acid binding agent.

Thus, the present invention relates to a process for the preparation of N-(2,6-dialkylphenyl)-N-methoxyacetyl-DL-alanine methyl ester derivative of the general formula (I),

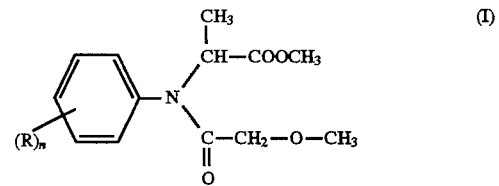

wherein
R stands for a $C_{1-4}$alkyl group, and and
n is 1, 2 or 3,
which comprises reacting an alkaline metal salt of an N-methoxyacetyl-2,6-dialkylaniline of the general formula (II),

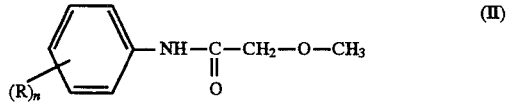

wherein R and n are as defined above, directly or after isolating it with the stoichiometric amount of methyl DL-α-halopropionate optionally in a solvent medium at a temperature between -20° C. and 50° C., preferably at 25° to 35° C. Organic solvents, mainly aromatic and/or cycloaliphatic solvents such as benzene, toluene, xylene, methylcyclohexane and the like are suitable solvents for this purpose. Methyl DL-α-chloro- or bromopropionate may be used as a methyl DL-α-halopropionate. The alkylation may be accomplished by using the previously isolated alkaline metal salt of the N-methoxyacetyl-2,6-dialkylaniline or alternatively, by preparing the alkaline metal salt of the N-methoxyacetyl-2,6-dialkylaniline in situ and then carrying out the alkylation according to the invention without isolating the salt.

The derivative of formula (I) can also be reacted with an N-methoxyacetyl derivative of formula (II), with a stoichiometric amount of an alkali metal alkoxide between 80° C. and 150° C., until the disappearance of the alkoxide, or until completion of the removal of the alkanol in the system, then reacting the thus obtained alkali metal salt of the compound of formula (II) directly or after isolation with a methyl DL-α-halopropionate.

The advantages of the process according to the invention can be summarized as follows:

1) Due to the absence of any acid binding agent in the alkylation, the process results in a pure product in a higher yield then obtained by means of the processes known.

2) To prepare one part of metalaxyl third or half part of the alkylating agent is required in comparison to the processes known in the art.

3) A substantially less amount of wastes loading the environment is produced in comparison to the processes known in the art. An alkaline metal halide is only formed as side product, which can be recyclized into the process after a suitable treatment.

4) The alkylation is carried out at a temperature between −20° C. and 50° C., preferably at 25° to 35° C. instead of a temperature between 120° C. and 140° C., which is very preferable from the processing point of view and results in a pure product.

The process according to the invention is illustrated in detail by the following non-limiting Examples.

EXAMPLE 1

Preparation of Metalaxyl 600 ml of xylene and 91 g of 0.5 molar sodium methoxide solution (containing 29.6% of sodium methoxide) were weighed in a flask fitted with a stirrer, thermometer and distillation device. The reaction mixture was heated to 140° C. and the leaving methanol was collected in a receiver. After reaching a temperature of 140° C. the reaction mixture was boiled under reflux for 30 minutes, then the boiling was stopped and 96.5 g (0.5 mol) of N-methoxyacetyl-2,6-dimethylaniline (hereinafter abbreviated: DMA-Ac) was added while allowing the mixture to cool to 120° C.

Thereafter the reaction mixture was heated to 140° C. while distilling off a fraction in order to maintain the boiling point of the mixture at 140° to 141° C. After boiling under reflux for 1 hour, the mixture was cooled to 30° C. and 94 g (0.55 mol) of methyl DL-α-bromopropionate were added to the suspension of N-methoxyacetyl-2,6-dimethylaniline sodium salt obtained. After maintaining the reaction mixture at 30° C. (under cooling) for 3 hours, the sodium bromide arising from the reaction was washed with water. The xylene solution was evaporated and liberated from the solvent under a reduced pressure of 5 kPa up to a final temperature of 125° to 130° C. After cooling the white melt weighed 130 g (93.5% yield), the purity of the product was 96.2%, m.p.: 70° C.

EXAMPLE 2

After the complete dissolution of 11.5 g of sodium metal in 100 ml of methanol 600 ml of xylene were added, then the process of Example 1 was followed to obtain 135 g of the aimed product (yield 94.6%) with a purity of 98.1%, m.p.: 71.5° C.

EXAMPLE 3

After dissolving 96.5 g (0.5 mol) of DMA-Ac in 600 ml of xylene, the xylene solution was heated to 130° C. and 27 g (0.5 mol) of solid sodium methoxide were added at the same temperature. After removal of the methanol Example 1 was followed which aimed a product in a yield of 132 g (92%).

EXAMPLE 4

Example 1 was followed, except that DMA-Ac was dissolved in 200 ml of xylene and portionwise added at 130° C. to the mixture of sodium methoxide in xylene. Thereafter, Example 1 was followed to obtain the aimed product in a yield of 132 g (91.5%) with a purity of 97%, m.p.: 71° C.

EXAMPLE 5

600 ml of xylene, 91 g (0.5 mol) of sodium methoxide and 96.5 g (0.5 mol) of DMA-Ac were weighed in the flask used in Example 1. The system was slowly heated to 65°–70° C. under a reduced pressure of 5 kPa. After removal of the methanol the reaction mixture was boiled under reflux at 70° C. for 1 hour, then Example 1 was followed to give the aimed product in a yield of 136 g (91.1%) with a purity of 93.8%, m.p.: 68° C.

EXAMPLE 6

Example 3 was followed, except that the system was cooled to 20° C. after disappearance of sodium methoxide. Then, after complete removal of the solvent in a vacuum dryer the product obtained was suspended in 400 ml of xylene and 94 g (0.55 mol) of methyl DL-α-bromopropionate were added at 30° C. Subsequently, the process was followed which is described in Example 3 to obtain the aimed product in a yield of 133 g (93%) with a purity of 97.5%, m.p.: 71° C.

EXAMPLE 7

Preparation of Metalaxyl (2,6-Dimethyl-N-(2-methyl-propionate)-N-methoxy-acetamide 900 ml of methylcyclohexane was weighed into a 2 liter flask equipped with stirrer, thermometer, distillation device and a descending cooler, further with a separator to recycle continuously the upper phase and removing of the lower phase. 94.5 g (0.55 mole) of NaOCH$_3$ was added in 30% solution. The methanol was removed by means of azeotropic distillation in a way that methyl cyclohexane has been continuously recycled into the system. 96.5 g of 2,6-dimethyl-N-methoxy-acetanilide was added and the formed methanol has been removed again. Thereafter 300 ml of solvent was distilled off to remove the last traces of methanol. The reaction mixture was cooled to 30° C. and during continuous cooling, keeping the temperature under 40° C. 94.5 g (0.6 mole) of α-bromo-propionic acid methyl-ester was added. After reacting the mixture 2 hours 180 ml of water was added and the mixture was cooled on −5° C.

The crystals precipitated has been filtrated, the product washed with water until free form NaBr traces and the crystals were dried on at most 50° C.

The crystals obtained weighed 130.5 g.

Purity: 98.8%. Melting point: 72° C.

Yield: 92.8%.

The 2 phases of the remained filtrate was removed and the methylcyclohexane contained 8.2 g of metalaxyl.

Yield: 128.9+8.2 g=137.1 g (98.6%).

EXAMPLE 8

900 ml of methylcyclohexane were weighed into a 2 liter flask equipped with stirrer, thermometer, distillation device, descending cooled and a separator suitable to remove the lower phase and recycling the upper phase. In the methylcyclohexane 96.5 g (0.5 mole) 2,6-dimethyl-N-methoxy-acetanilide was dissolved. The mixture was warmed until 80° C. Thereafter a 30% methanolic solution of 94.5 g (0.5 mole) $NaOCH_3$ was added in a slow rate. After the total removal of methanol the process was carried out as according to Example 1 with the difference that the dissolving of NaBr with water from the reaction mixture was effected at 5° C.

The product weighed 133 g.
Purity: 99.1%.
Melting point: 72° C.
Yield: 94.6%.

The 2 phases of the remained filtrate was separated and on processing it the methyl cyclohexane solvent contained 7.5 g of metalaxyl.

Total yield: 132.4 g+7.5 g=138.1 (99.2%).

EXAMPLE 9

94.5 g (0.55 mole) of $NaOCH_3$ in form of 30% solution was weighed into a 2 liter flask equipped with stirrer, thermometer, distillation device and a separator suitable to remove the upper phase and recycling the lower phase. Into the flask 94.5 g (0.55 mole) of $NaOCH_3$ was weighed in 30% methanolic solution and 96.5 g (0.5 mole) of 2,6-dimethyl-N-methoxy-acetanilide was dissolved in this solution. The methanolic solution of the sodium salt of 2,6-dimethyl-N-methoxy-acetanilide was added to 900 ml of methylcyclohexane kept on 80° C. The azeotropic mixture of methylcyclohexan and methanol distilling off the flask was cooled and the obtained phases were separated. The upper phase of methylcyclohexane was recycled to the reaction mixture until the top temperature of the fraction reaches the boiling temperature of methylcyclohexane (101° C.). Thereafter about one third of the solvent (200 ml) was distilled off from the reaction mixture. The suspension of sodium salt of 2,6-dimethyl-N-methoxy-acetanilide in methyl cyclohexane was cooled on 30° C. and 94.5 g (0.6 mole) of α-bromo-propionic acid methyl-ester was added and the mixture was reacted 2 hours on the same temperature while the mixture was continuously cooled. Thereafter 180 ml of water was added to the mixture and it was cooled on −5° C. The separated metalaxyl was filtrated, it was washed with water and dried. The product weighed 129 g.

Purity: 99.2%.
Melting point: 72° C.
Yield: 92.2%.

The 2 phases of the remained filtrate was separated and from the organic phase—which was methylcyclohexane—further 8 g of metalaxyl could be isolated.

Total yield: 129 g+8 g=137 g (98.3%).

EXAMPLE 10

Preparation of the Sodium Salt of 2,6-Dimethyl-N-methoxy-acetanilide 800 ml of methylcyclohexane was weighed into a flask equipped with a stirrer, thermometer, reflux head and a receiver—which latter served as a separator and 96.5 g of 2,6-dimethyl-N-methoxy-acetanilide and 94.5 g of $NaOCH_3$ in 30% methanolic solution was added. The methanol was distilled off the mixture. The methanol forms with the methylcyclohexane an azeotropic mixture having a very low boiling point of 59.2° C. The distillation of methanol was continued until the temperature rose in the reflux head to 102° C. During this time the methylcyclohexane and the methanol separates into 2 phases. The upper phase was recirculated continuously into the reactor. When the temperature of the head rose to 102° C. then the sodium salt of 2,6-dimethyl-N-methoxy-acetanilide precipitates from the solution in form of a white precipitate. Thereafter a third part of the methylcyclohexane was distilled off. The reaction mixture was then cooled to 0° C., the precipitate was filtrated under nitrogen gas then the precipitate was washed with methylcyclohexane, finally the precipitate was dried under nitrogen gas. The product weighed 105 g.

Yield 97.2%.

Analytical data:

| Calculated | measured |
| --- | --- |
| C: 61.40% | C: 61.54% |
| H: 6.51% | H: 6.47% |
| N: 6.51% | N: 6.43% |
| Na: 10.70% | Na: 10.61% |
| O: 14.88% | O: 14.95% |

We claim:
1. Process for the preparation of N-phenyl-N-methoxyacetyl-DL-alanine methyl ester derivatives of the general formula (I),

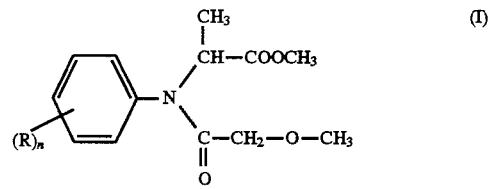

wherein
R stands for a $C_{1-4}$alkyl group; and
n is 1, 2 or 3,
which comprises reacting an N-methoxyacetyl derivative of the general formula (II),

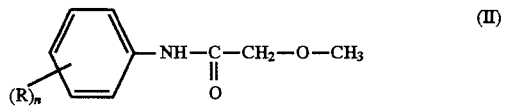

wherein R and n are as defined above, with a stoichiometric amount of an alkaline metal alkoxide, at a temperature of 80° C. to 150° C., until the disappearance of the alkoxide or until completion of the removal of the alkanol being present in the system, then reacting the thus obtained alkaline metal salt of the compound of general formula (II) directly or after isolation with a methyl DL-α-halopropionate.

2. A process according to claim 1 which comprises performing the reaction between −20° C. and +50° C.

3. A process according to claim 1 using as solvent aromatic and/or cycloaliphatic solvents.

4. A process according to claim 1 which comprises reacting methyl-Dl-α-halopropionate in a molar ratio of about 1.1:1 calculated on the N-methoxyacetyl derivative of general formula (II).

5. The process of claim 1 which comprises performing the reaction between 25° C. and 35° C.

6. The process of claim 1, wherein one or more of benzene, toluene, xylene, and methylcyclohexane is used as a solvent.

* * * * *